United States Patent
Kirchhoff et al.

(10) Patent No.: US 7,037,896 B1
(45) Date of Patent: May 2, 2006

(54) PEPTIDE (VIRIP) WHICH INHIBITS A CIRCULATING VIRUS IN HUMANS AND THE USE THEREOF

(75) Inventors: Frank Kirchhoff, Erlangen (DE); Jan Münch, Erlangen (DE); Ludger Ständker, Hannover (DE); Wolf-Georg Forssmann, Hannover (DE)

(73) Assignee: IPF PharmaCeuticals GmbH, Hannover (DE)

( * ) Notice: Subject to any disclaimer, the term of this patent is extended or adjusted under 35 U.S.C. 154(b) by 31 days.

(21) Appl. No.: 10/111,427

(22) PCT Filed: Nov. 8, 2000

(86) PCT No.: PCT/EP00/11020

§ 371 (c)(1),
(2), (4) Date: Oct. 15, 2002

(87) PCT Pub. No.: WO01/34640

PCT Pub. Date: May 17, 2001

(30) Foreign Application Priority Data

Nov. 8, 1999 (DE) ................................ 199 53 732
May 16, 2000 (DE) ................................ 100 23 665

(51) Int. Cl.
*A61K 38/16* (2006.01)
*C07K 7/08* (2006.01)
*C07K 2/00* (2006.01)
*A61K 38/00* (2006.01)
*A61K 38/02* (2006.01)

(52) U.S. Cl. ............... 514/13; 514/2; 514/7; 514/8; 530/300; 530/326

(58) Field of Classification Search ............ 514/2, 514/13; 530/300, 326

See application file for complete search history.

(56) References Cited

U.S. PATENT DOCUMENTS

| 5,420,110 A | 5/1995 | Miller |
| 5,827,662 A | 10/1998 | Rubin et al. |
| 5,972,901 A * | 10/1999 | Ferkol et al. ............... 514/44 |

FOREIGN PATENT DOCUMENTS

| EP | 0 114 777 | 8/1990 |
| EP | 0 511 188 | 6/1997 |
| WO | WO 84/02918 | 8/1984 |
| WO | WO 97/46100 | 12/1997 |
| WO | WO 01/08708 | 2/2001 |

OTHER PUBLICATIONS

J Rudinger. In: Peptide Hormones, JA Parsons, Ed. (1976), 1-7.*
DE Smilek, et al. Proc. Natl. Acad. Sci. USA (1991) 88, pp. 9633-9637.*
D Voet and JG Voet. "Abnormal Hemoglobins" in Biochemistry, 2Ed. (1995). pp. 235-241.*
Buchwalder et al., "EMBL:A35541"—XP-002164956, Jul. 3, 2001.
Shapiro et al., "Alpha-1-antitrypsin inhibits human immunodeficiency virus type 1", FASEB Journal, vol. 15, 122, Jan. 2001, pp. 115-122.

* cited by examiner

*Primary Examiner*—Bruce R. Campell
*Assistant Examiner*—Andrew D. Kosar
(74) *Attorney, Agent, or Firm*—Jacobson Holman PLLC (57) ABSTRACT

A peptide having the following amino acid sequence:

$$Z_1\text{-LEAIPMSIPPEVKFNKPFVF-}Z_2 \text{ (VIRIP)}$$

and its biologically active fragments and/or variants and/or derivatives, especially amidated, acetylated, sulfated, polyethylene glycol (PEG) modified, phosphorylated and/or glycosylated derivatives, and peptides obtainable by multiple synthesis which have the biological activity of VIRIP; wherein $Z_1$ and $Z_2$ are independently a sequence of from 0 to 10 amino acid residues, and if $Z_1$ or $Z_2$=zero amino acid residues, then $Z_1$=H and/or $Z_2$=COOH.

4 Claims, 5 Drawing Sheets

| Isolate: | V3 sequence | % cont. | charge | trop. |
|---|---|---|---|---|
| P59-S/27 | ---- gspq-r--r- ..-----wlw yargng------ --- | 98 | +7 | X4 |
| P34-S | ---- --his-r-s- ..------ra -er-..-----k --- | 91 | +8 | X4 |
| 92ht593-1 | ---- ----s-r-s- ..------ra -.k-..--n--- ---90 | | +7 | X4/R5 |
| HXB2 | ---- ------r-r- --------v- i-k-...-nm-- --- | 90 | +9 | X4 |
| 93br020-17 | ---- ------r-sl ..----v--- a---..-----k ---88 | | +7 | X4/R5 |
| P51-S | ---- g-k--r-ms- ..------ia -rq-..-----k --- | 85 | +7 | X4/R5 |
| 92rw020-5 | ---- ------gvr- ..---q---a --g-..------ --- | 78 | +5 | R5 |
| 011jr103 | ---- --------p- ..-------- ----..------ --- 75 | | +6 | R5 |
| LAI | ---- --------r- ---------- i-k-...--nm-- --- | 70 | +8 | X4 |
| NL43 | ---- --------r- --------v- i-k-...-nm-- --- | 70 | +8 | X4 |
| 93br025-9 | ---- --------r- ..---q---a ----..------ ---58 | | +5 | R5 |
| YU2 | ---- --------n- ..-----l-- ----..------ --- 50 | | +5 | R5 |
| 005pf135 | ---- ------g--- ..-------- ----..------ --- 28 | | +5 | R5 |
| SG3.1 | ---- -kk---r-tt ..----vy-- ----..v----- --- | 30 | +8 | X4/BOB |
| 92th014-12 | ---- ---------l ..-----w-- --q-..------ ---22 | | +5 | R5 |
| Consensus | CTRP NNNTRKSIHI QRGPGRAFYT TGEI..IGDIRQ AHC | | | |

PEPTIDE (VIRIP) WHICH INHIBITS A CIRCULATING VIRUS IN HUMANS AND THE USE THEREOF

This is a 371 of PCT/EP00/11020 filed Nov. 8, 2000, the disclosure of which is incorporated herein by reference.

The present invention relates to a polypeptide (protein) having inhibiting properties on the viral infection of cells: human virus-inhibiting peptide (VIRIP) and its therapeutic and diagnostic use. The invention comprises the naturally occurring form of VIRIP as well as fragments and/or analogues derived therefrom or derivatives, and finally a medicament containing the natural, recombinant and synthetic peptides to be used for medical indications and to be used as a diagnostic agent. In addition, the invention relates to modified forms of VIRIP which have a particularly favorable therapeutic effectiveness. It further relates to a nucleic acid probe hybridizing to VIRIP or one of its fragments and/or derivatives, and antibodies and antagonists directed against VIRIP or one of its fragments and/or derivatives for diagnostic or therapeutic use, especially in viral diseases and for the treatment of HIV-1 and HIV-2 infections.

Surprisingly, VIRIP could be isolated from human hemofiltrate by chromatographic methods and using a biological assay. The biochemical characterization of the peptide according to the invention was performed by mass spectrometry and the complete sequencing of all amino acids.

The peptide has the following amino acid sequence:
$Z_1$-LEAIPMSIPPEVKFNKPFVF-$Z_2$(SEQ ID NO: 1), wherein $Z_1$ and $Z_2$ are independently a sequence of from 0 to 10 amino acid residues, and if $Z_1$ or $Z_2$=zero amino acid residues, then $Z_1$=H and/or $Z_2$=COOH.

The molecular mass of the VIRIP peptide according to the invention is 2303 Da when $Z_1$ and $Z_2$ mean no amino acid residues.

As derivatives of VIRIP, there may be mentioned, in particular, amidated, acetylated, sulfated, polyethylene glycol (PEG) modified, phosphorylated and/or glycosylated derivatives, and the peptides obtainable by multiple synthesis which have the biological activity of VIRIP.

The peptide according to the invention comprises a fragment of 20 amino acids of the known human protein alpha-1-antitrypsin (Accession No. P01009), which in its processed form consists of 394 amino acids. The function of the alpha-1-antitrypsin is predominantly described as an inhibitor of the enzymes elastase as well as thrombin and plasmin. The peptide sequence of VIRIP according to the invention preferably begins behind amino acid 352 of alpha-1-antitrypsin and thus comprises the amino acids 353 to 372 of alpha-1-antitrypsin.

Surprisingly, the peptide according to the invention causes a suppression of HIV-1 infection and/or replication of or in human blood cells.

The peptide according to the invention can be obtained by a purification method starting from human hemofiltrate. This hemofiltrate is obtained in large amounts in the ultrafiltration of the blood of patients suffering from kidney diseases.

The invention also relates to polynucleotides coding for the peptide according to the invention, such polynucleotides being preferably constituted of DNA, RNA, genomic DNA or PNA. Another aspect of the invention relates to vectors containing the polynucleotides according to the invention, and genetically engineered host cells containing the vector according to the invention. The invention also relates to polynucleotides which will hybridize to the polynucleotides according to the invention (antisense nucleotides). Further aspects of the invention relate to antibodies directed against the peptides according to the invention, and antagonists and inhibitors which inhibit the activity of the peptides according to the invention.

The peptide according to the invention may also be coupled to an adaptor protein which ensures uptake into virus-infectable cells.

The invention also relates to methods for the treatment of patients in need of VIRIP by administering therapeutical quantities of the polypeptides according to the invention, and methods for the treatment of patients in need of VIRIP inhibition by administering therapeutical quantities of an antagonist/inhibitor.

Alternatively, the therapeutical effect of the polypeptide according to the invention can be achieved by administering polynucleotides coding for VIRIP, followed by in vivo expression in the patient.

The human hemofiltrate is optionally diluted with water and acidified. The pH value is preferably from 1.5 to 3.5, especially from 2.5 to 3.0. Thereafter, the hemofiltrate is passed through a cation exchanger, for example, a support material modified with sulfonic acid groups (Fractogel SP-650 (M), Merck, Darmstadt). The peptides bound to the cation exchanger are eluted with a relatively high concentration of a salt solution. The ionic strength of the eluant is about that of a 0.5 to 1 M ammonium acetate solution.

The collected eluate is subjected to another cation exchange chromatography. This chromatography is preferably a fractional elution with buffers having increasing pH values.

The fractions containing the peptide according to the invention are further purified by preparative reverse-phase chromatography followed by semipreparative reverse-phase chromatography, for example, on C18-modified support materials. The degree of purification is preferably monitored using analytical reverse-phase chromatography, for example, on C18-modified support materials.

The substance obtained by the chromatographic purification was subjected to structural elucidation. The determination of the molecular masses of the purified peptide was effected by means of an electrospray mass spectrometer (ESI-MS). The sequence analysis of the native peptide was performed through Edman degradation with an ABI 473 A sequencer. The peptide sequence according to the invention was synthesized chemically, and the structure of the synthetically prepared peptide was also elucidated. This synthetically prepared VIRIP also causes a dose-dependent suppression of HIV-1—infection and/or replication of or in human blood cells.

The peptide according to the invention and its cDNA, its gene and analogues, fragments and derivatives of the peptide, of the cDNA and of the gene, as well as antibodies which neutralize the activity of VIRIP can be employed as medicaments. Its biological activity corresponds to that of virus-inhibiting substances. It can be assumed that VIRIP is taken up into the blood cells due to its short hydrophobic sequence, where it acts as an inhibitor of viral enzymes or as an inhibitor of enzymes of the blood cells, or that VIRIP binds to receptors which play a role in the entry of viruses. Thus, VIRIP prevents the infection of cells with the virus.

The peptide according to the invention can be administered in a way usual for peptides on a parenteral, intravenous, intramuscular, intranasal, local-topic, subcutaneous or buccal route. The amount of peptide to be administered is from 1 mg to 1 g per unit dose per day. The activity of the peptide according to the invention can be inhibited by administering appropriate inhibitors/antagonists.

The diagnostic agent according to the invention contains poly- or monoclonal antibodies against the peptide according to the invention, optionally in a fluorescence-labeled or radioactively labeled form, to be employed in a per se known ELISA or RIA. The antibodies against a peptide according to the invention can be obtained by the immunization of mammals. The diagnostic agent according to the invention contains DNA, RNA and/or PNA, optionally in a modified and/or labeled form, for use in test systems known to the skilled person, such as PCR or fingerprinting.

The invention will now be further described by means of the following Examples.

EXAMPLE 1

Isolation of the Antivirally Effective VIRIP

1st Step: Hemofiltrate Batch Extraction

From 800 to 1000 liters of hemofiltrate is adjusted to a pH value of 2.7 with HCl and diluted with water to a conductivity of 5.5 mS/cm, and charged onto a strong cation exchanger with a flow rate of 3 l/min.

| Chromatographic conditions: | |
|---|---|
| Column: | Vantage VA 250 (Amicon, Witten, Germany) |
| Column material: | Fractogel TSK SP 650 (M), 25 cm × 20 cm |
| Flow: | 3 l/min |
| Detection: | 280 nm, pH, conductivity |
| Buffer A: | Hemofiltrate pH 2.7, conductivity 5.5 mS/cm |
| Buffer B: | 0.5 M ammonium acetate |
| Equipment: | Autopilot Chromatographic System (PerSeptive Biosystems, Wiesbaden, Germany) |

After charging the total of 1,000 liters of liquid over night, rinsing is effected with several column volumes of 5 mM HCl. The elution of the bound peptides is effected as a batch elution with 0.5 M ammonium acetate. A complete elution of the peptides is achieved through a ramping pH value (6.8 to 7.2) and ramping conductivity (56 mS/cm) in about 5 liters of eluate.

2nd Step: First Preparative Separation (Charge 01/1998)

The ammonium acetate eluates of the batch extraction are combined in an amount of 10,000 liters of hemofiltrate peptide. After adjusting the pH to 2.7, the peptide extract is charged onto the preparative cation exchanger with the addition of completely desalted water having a conductivity of 5.5 mS/cm.

| Chromatographic conditions: | |
|---|---|
| Column: | Vantage 250 VA |
| Column material: | Fractogel TSK SP 650 (M), 25 cm × 20 cm |
| Flow: | up to 3 l/min during the charging |
| | 0.5 to 1 l/min during the elution |
| Detection: | 280 nm, pH, conductivity |
| Sample: | Hemofiltrate pH 2.7, conductivity 5.5 mS/cm |
| Equipment: | Autopilot Chromatographic System (PerSeptive Biosystems, Wiesbaden, Germany) |

After charging the raw extract over 240 min, the column is rinsed with 0.01 M HCl until the conductivity is below 1 mS/cm. Elution is performed in several steps with the buffers stated below.

| Buffer | pH value | Buffer substances | Conductivity (mS/cm) |
|---|---|---|---|
| Washing buffer | 2.0 | 0.01 M HCl | |
| Elution buffer 1 | 3.6 | 0.1 M citric acid monohydrate | |
| Elution buffer 2 | 4.5 | 0.1 M acetic acid + 0.1 M sodium acetate | |
| Elution buffer 3 | 5.0 | 0.1 M malic acid | |
| Elution buffer 4 | 5.6 | 0.1 M succinic acid | |
| Elution buffer 5 | 6.6 | 0.1 M NaH$_2$PO$_4$ | |
| Elution buffer 6 | 7.4 | 0.1 M NaH$_2$PO$_4$ | |
| Elution buffer 7 | 9.0 | 0.1 M ammonium carbonate | |

Figure 1:
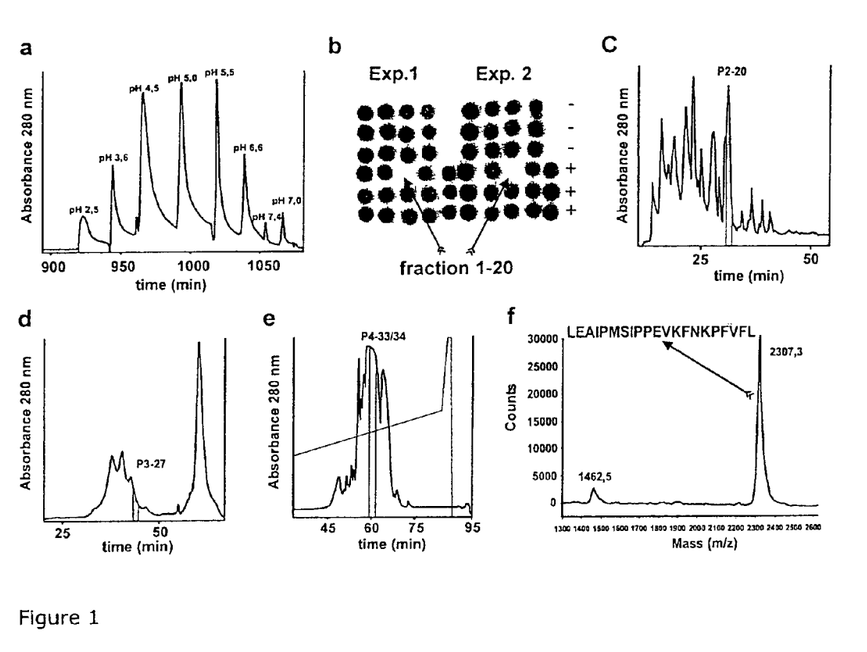
FIG. 1: Purification of VIRIP. The purification steps are described in the text. (b) Inhibition of the replication of HIV-1 NL43 in human blood lymphocytes by fraction 1–20. The cells were stimulated with PHA for 2 days, infected with virus stocks containing 10 ng of p24, and the reverse transcriptase activity determined in the culture supernatant 9 days after the infection. The result of the infection experiments is shown.

Eluates 1–7 are designated as pH pool I–VII (see FIG. 1a). They are separately collected and finally rinsed with completely desalted water. Elution is effected until a new base line is reached, elution volumes of from 10 to 25 liters being reached for the individual pH pools I to VII.

3rd Step: Second Preparative Separation:

The individual pH pools are separated by reverse-phase chromatography for fractionating and simultaneous desalting.

| Chromatographic conditions: | |
|---|---|
| Column: | FineLine 100 (Pharmacia, Freiburg, Germany) |
| Column material: | Source RPC, 15 µm |
| | 10 × 12.5 cm (FineLine 100) |
| Flow: | 150 ml/min (FineLine 100) |
| Detection: | 280 nm, conductivity, pH |
| Buffer A: | 10 mM HCl |
| Buffer B: | 80% acetonitrile in 10 mM HCl |
| Gradient: | 0–60% buffer B in 5 column volumes |

After charging the individual pH pools, the column is washed with buffer A. During elution, fractions of 200 ml are collected. The fractions are freeze-dried and stored at −20° C. Aliquots of the fractions formed are tested in a bioassay. Fraction 20 from pH pool I contained the peptide according to the invention (see FIG. 1b, c).

4th Step: Semipreparative Reverse-Phase C18 Chromatography:

A total of 500 mg of fraction 20 from pH pool I, which was bioactive in the assay, was separated through a semipreparative reverse-phase column. Fraction 27 contained the substance according to the invention (see FIG. 1d).

| Chromatographic conditions: | |
|---|---|
| Column: | 4.7 cm × 30 cm steel column |
| Packing material: | Vydac RP-C18 15–20 µm, 300 X |
| Buffer A: | 30% methanol, 70% water, 0.1% TFA |
| Buffer B: | 100% methanol, 0.1% TFA |
| Gradient: | 0–60% B in 2100 ml |
| Flow: | 40 ml/min |
| Detection: | 214 nm and 280 nm |
| Chromatographic equipment: | BioCad 250, Perseptive Biosystems |
| Fractions: | 50 ml each from start of gradient |

5th Step: Analytical Reverse-Phase C4 Chromatography:

The bioactive fraction 27 from the previous chromatography was separated through an analytical reverse-phase column. Aliquots were tested in a bioassay. Fractions 33 and 34 contained the substance according to the invention in a purified form.

| Chromatographic conditions: | 5 µm, 100 X, 20 × 250 mm |
|---|---|
| Column: | 2 cm × 25 cm steel column |
| Packing material: | RP-C4, 5 µm, 100 X, Biotek Silica, Östringen, Germany |
| Buffer A: | water, 0.1% TFA |
| Buffer B: | 80% acetonitrile, 20% water, 0.1% TFA |
| Gradient: | 20–60% B in 80 min, 60–100% B in 2 min |
| Flow: | 8 ml/min |
| Detection: | 214 nm and 280 nm |
| Chromatographic equipment: | Kontron |
| Fractions: | 1.5 min each from start of gradient |

Thereupon, the pure substance according to the invention was examined in a bioassay in a dose-dependent manner and characterized by peptide chemistry.

EXAMPLE 2

Mass Determinations

The mass determinations on the peptide isolated from hemofiltrate (from fractions 33 and 34 of the 5th step in Example 1) and on the chemically synthesized peptide (Example 3) were performed on an ESI mass spectrometer (see FIG. 1f). The molecular masses of the peptides were determined to correspond to the following mass figures (MW):

| VIRIP, isolated from human hemofiltrate: | 2303 Da |
|---|---|
| VIRIP, chemically synthesized peptide: | 2303 Da |

Sequence Determination

The purified native and chemically synthesized peptides were analyzed by means of Edman degradation on an ABI 473 A sequencer using the standard program. The samples were charged on a polybrene membrane in amounts of between 100 and 400 pmol. Both for the peptide isolated from hemofiltrate (from fractions 33 and 34 of the 5th step in Example 1) and for the chemically synthesized peptide (Example 3), the following complete amino acid sequence was identically found:

LEAIPMSIPPEVKFNKPFVF

Data Base Comparison

A data base comparison was performed using the HUSAR program package on the SwissProt and EMBL data bases. The peptide sequence has 100% identity with amino acids 353–372 of the human protein alpha-1-antitrypsin (Accession No. P01009) as derived from its cDNA.

EXAMPLE 3

Chemical Synthesis of VIRIP

The chemical synthesis of VIRIP was performed by means of conventional solid-phase synthesis on a peptide synthesizer 9050 using the known Fmoc chemistry. The peptide obtained was purified by reverse-phase chromatography, and its identity and purity were established by analytical RP-HPLC and by the mass and sequence determination as described under Example 2.

EXAMPLE 4

Determination of the Antiviral Activity of VIRIP

The isolation of VIRIP was effected on the basis of its inhibitory action on the replication of HIV-1 in an assay which measures the replication of HIV-1 in human peripheral blood lymphocytes (PBMCs). Thus, aliquots of each of the individual chromatographic fractions described under Example 1 were freeze-dried and then subjected to the biological assay in amounts of from 10 ml up to 1 l of hemofiltrate equivalent. The respective fractions which gave a positive signal were subjected to further purification.

Human peripheral blood lymphocytes (PBMCs) were obtained from whole blood using density gradient centrifugation in Ficoll. The cells were prestimulated for two days (RPMI medium, 20% FKS, 100 U/ml IL-2, 5 µg/ml phytohemagglutinin [PHA]). Then, the PBMCs were sedimented by centrifugation at 1200 rpm for 5 min, taken up in PHA-free RPMI medium (20% FKS, 100 U/ml IL-2) and seeded in 96-well flat-bottomed plates in a volume of 80 μl in concentrations of about 150,000 cells per well.

On the following day, aliquots of the individual chromatographic steps described under Example 1 were supplied in amounts of from 10 ml up to 1 l of hemofiltrate equivalent. Thus, the freeze-dried chromatographic fractions were taken up in water and pipetted to the PBMCs in various concentrations in a total volume of 10 μl. After 2 hours of incubation at 37° C., the cells were infected by the addition of 10 μl of HIV-1 virus stock containing from 0.1 to 10 ng of p24 antigen. Subsequently, 50 μl of the culture medium was replaced every 2 days by fresh medium which additionally contained the corresponding peptide fractions. The production of HIV particles at different times (after 9, 12 and 18 days) from the infection of the cells was quantified in a reverse transcriptase (RT) test. The RT test measures the activity of reverse transcriptase in a cell-free culture supernatant, which is thus a measure of the production of viral particles and viral replication in the PBMC cultures. Alternatively, the viral production was determined in p24 antigen ELISA. Fractions which resulted in at least 90% reduction of RT production as compared with mixtures lacking potentially stimulating or inhibitory peptides (see FIG. 1b, for example) and thus inhibited the replication of HIV-1 in human PBMC efficiently were further purified.

Figure 2:
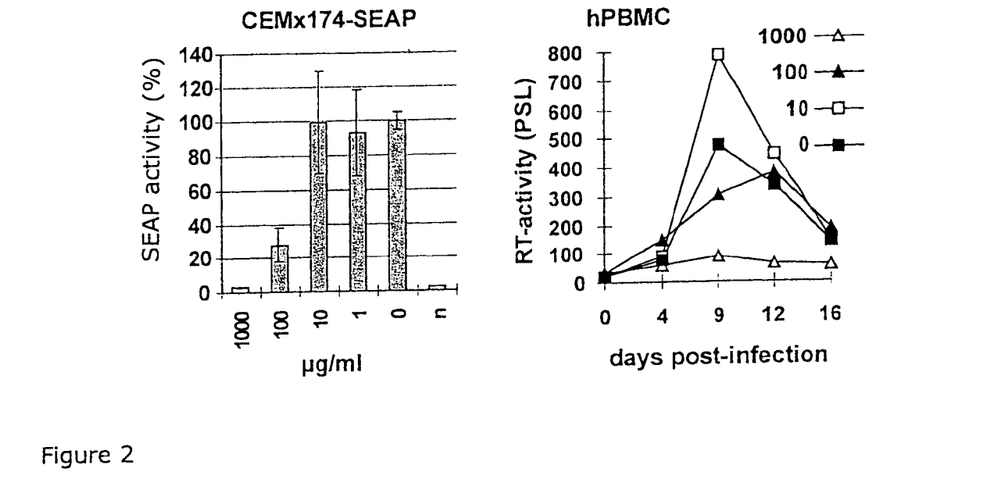
FIG. 2: Influence of synthetic VIRIP on the infection of CEMx174-SEAP indicator cells (left) and replication in human PBMCs (right). The cells were infected and cultured in the presence of the stated amounts of VIRIP. To determine the viral entry, the activity of the secreted alkaline phosphatase was determined in the culture supernatant of the CEMx174-SEAP cells three days after the infection.

Both the VIRIP purified from hemofiltrate (Example 1) and the chemically synthesized VIRIP (Example 3) exhibited a dose-dependent inhibition of the HIV-1 infection of CEMx174-SEAP indicator cells and of the replication in PBMCs (FIG. 2). In contrast, the VIRIP according to the invention does not exert any cytotoxic effect on the blood cells.

EXAMPLE 5

The efficiency of VIRIP-specific inhibition depends on the sequence of the V3 loop in the HIV-1 envelope protein.

Figure 3:
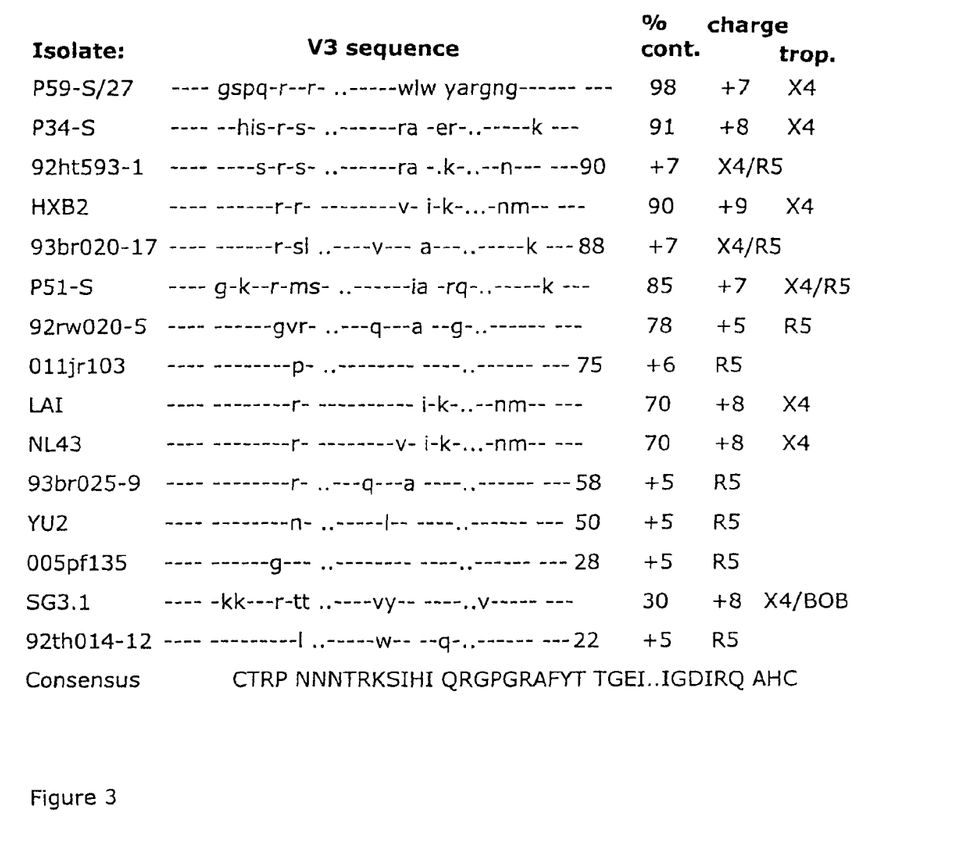
FIG. 3: The V3 loop of the X4-tropic NL43 clone was exchanged for the corresponding sequences of the HIV-1 isolates shown. Thus, the recombinant viruses are distinguished exclusively in the V3 loop. In the right panel, the observed inhibitors effect (%), the overall charge of the V3 region and the co-receptor-tropism are shown. At the bottom, the consensus sequence (SEQ ID NO: 6) is shown.

The results demonstrated that both VIRIP from hemofiltrate and the synthetically prepared peptide effectively block the replication of HIV-1 NL43. In order to establish whether VIRIP is specific for X4-tropic variants or also inhibits other forms which utilize the co-receptor CCR5 or are dual-tropic (X4/R5), a number of V3 variants of the molecular NL4-3 clone were examined (FIG. 3). The V3 loop of the X4-tropic NL4-3 clone was replaced by the corresponding region of a number of primary HIV-1 isolates. Functional tests with different indicator cell lines showed that these V3 recombinants have different cell and co-receptor tropisms. To determine the inhibitory influence of VIRIP on these variants, P4R5 indicator cells were examined. P4R5 cells express both CCR5 and CXCR4 and contain the luciferase gene under the control of HIV-1 LTR. This cell line was infected with the various recombinant viruses (50 ng of p24) in the presence and absence of VIRIP, and the infection was quantified using the luciferase test. As shown in FIG. 3, VIRIP inhibited X4-tropic as well as R5-tropic and X4/R5-tropic variants. All in all, however, X4-tropic variants having a strongly positively charged V3 loop were inhibited more efficiently as compared with R5-tropic or dual-tropic isolates.

Figure 4:
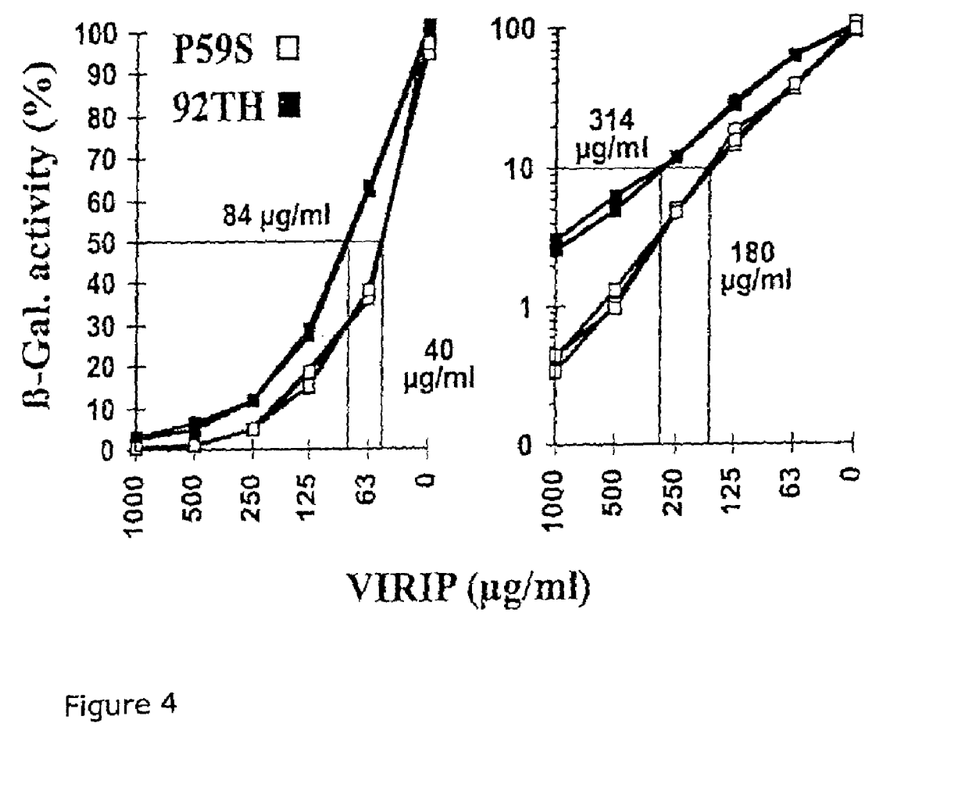
FIG. 4: Dose-dependent inhibition of the X4-tropic P59S and R5-tropic 92TH HIV-1 NL4-3 recombinants by VIRIP. P4R5 indicator cells were infected in the presence of the shown concentrations of VIRIP, and the β-galactosidase activity was measured in the cell extract 2 days after the infection.

In order to quantify the inhibitory effect of the substance according to the invention more precisely, P4R5 indicator cells were infected with the X4-tropic HIV-1 P59S isolate and the R5-tropic 92TH isolate in the presence of different doses of VIRIP. As shown in FIG. 4, VIRIP inhibited the HIV-1 P59S isolate by 50% at a concentration of 40 μg/ml, and by 90% at a concentration of 180 μg/ml. For inhibiting the X-tropic 92TH isolate, about twofold higher concentrations of VIRIP were required (FIG. 4).

Figure 5:
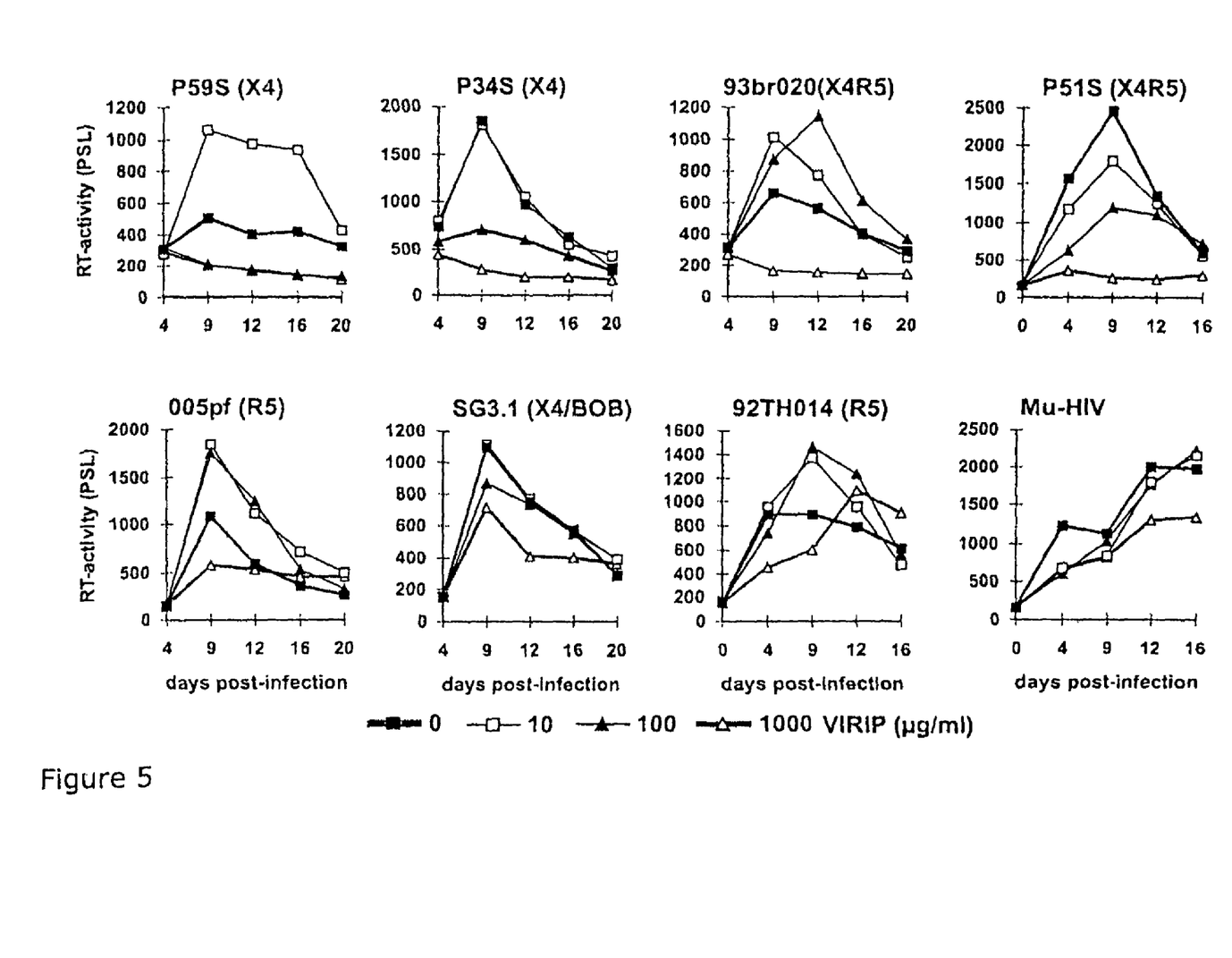
FIG. 5: VIRIP inhibits the replication of various HIV isolates with different cell- and co-receptor-tropisms in human PBMC. Prestimulated PBMC were treated with the various HIV-1 isolates (10 ng of p27 antigen) or a chimeric onco-lentivirus (Mu-HIV) in the presence of the VIRIP concentrations shown. Viral replication was determined by measuring the reverse transcriptase activity in the cell culture supernatant.

In further experiments, it was shown that VIRIP suppresses the replication of X4-tropic and dual-tropic HIV variants in human PBMC completely at concentrations of 1000 μg/ml and at least partially at concentrations of 100 μg/ml (FIG. 5, top). The inhibitory effects on R5-tropic forms were lesser. A chimeric onco-lentivirus (Mu-HIV) carrying the MLV envelope protein was not inhibited (FIG. 5, bottom).

The invention claimed is:

1. A synthesized or isolated virus-inhibiting peptide consisting of the amino acid sequence LEAIPMSIPPEVKFNKPFVF (SEQ ID NO: 1) or one of its amidated, acetylated, sulfated, polyethylene glycol (PEG) modified, phosphorylated or glycosylated derivatives which has biological inhibiting activity against HIV-1 and/or HIV-2.

2. A synthesized, isolated, or heterologously expressed virus-inhibiting peptide selected from the group consisting of:
   a) the amino acid sequence LEAIPMSIPPEVKFNKPFVF (SEQ ID NO: 1) and
   b) an amidated, acetylated, sulfated, polyethylene glycol (PEG) modified, phosphorylated or glycosylated derivative thereof, wherein the peptide suppresses HIV-1 and/or HIV-2 infection and/or replication in human blood cells.

3. A medicament containing the peptide according to claim 1 together with a compatible carrier in a galenic formulation.

4. A medicament containing the peptide according to claim 2 together with a compatible carrier in a galenic formulation.

* * * * *

UNITED STATES PATENT AND TRADEMARK OFFICE
CERTIFICATE OF CORRECTION

PATENT NO. : 7,037,896 B1  
APPLICATION NO. : 10/111427  
DATED : May 2, 2006  
INVENTOR(S) : Frank Kirchhoff et al.

It is certified that error appears in the above-identified patent and that said Letters Patent is hereby corrected as shown below:

Title Page item 54, and column 1, lines 1-3 change the title from "PEPTIDE (VIRIP) WHICH INHIBITS A CIRCULATING VIRUS IN HUMANS AND THE USE THEREOF" to --CIRCULATING PEPTIDE (VIRIP) WHICH INHIBITS A VIRUS IN HUMANS AND THE USE THEREOF--.

Column 5, 2nd table, line 2, change "Vydac RP-C18 15-20 :m, 300 X)" to --Vydac RP-C18 15-20 :m, 300 Å)--;  
3rd table, insert title --Chromatographic conditions:-- above the table;  
3rd table, delete line 1; 3rd table, line 3, change "RP-C4, 5 :m, 100 X" to --RP-C4, 5 :m, 100 Å--.

Signed and Sealed this

Nineteenth Day of February, 2008

JON W. DUDAS  
*Director of the United States Patent and Trademark Office*

SEQUENCE LISTING

```
<160> NUMBER OF SEQ ID NOS: 6

<210> SEQ ID NO 1
<211> LENGTH: 20
<212> TYPE: PRT
<213> ORGANISM: Homo sapiens

<400> SEQUENCE: 1

Leu Glu Ala Ile Pro Met Ser Ile Pro Pro Glu Val Lys Phe Asn Lys
1               5                   10                  15

Pro Phe Val Phe
            20

<210> SEQ ID NO 2
<211> LENGTH: 21
<212> TYPE: PRT
<213> ORGANISM: Homo sapiens

<400> SEQUENCE: 2

Leu Glu Ala Ile Pro Met Ser Ile Pro Pro Glu Val Lys Phe Asn Lys
1               5                   10                  15
```

```
-continued

Pro Phe Val Phe Leu
            20

<210> SEQ ID NO 3
<211> LENGTH: 4
<212> TYPE: PRT
<213> ORGANISM: Human immunodeficiency virus

<400> SEQUENCE: 3

Gly Ser Pro Gln
1

<210> SEQ ID NO 4
<211> LENGTH: 9
<212> TYPE: PRT
<213> ORGANISM: Human immunodeficiency virus

<400> SEQUENCE: 4

Trp Leu Trp Tyr Ala Arg Gly Asn Gly
1               5

<210> SEQ ID NO 5
<211> LENGTH: 28
<212> TYPE: PRT
<213> ORGANISM: Artificial Sequence
<220> FEATURE:
<223> OTHER INFORMATION: Consensus Sequence

<400> SEQUENCE: 5

Cys Thr Arg Pro Asn Asn Asn Thr Arg Lys Ser Ile His Ile Gln Arg
1               5                   10                  15

Gly Pro Gly Arg Ala Phe Tyr Thr Thr Gly Glu Ile
            20                  25

<210> SEQ ID NO 6
<211> LENGTH: 9
<212> TYPE: PRT
<213> ORGANISM: Artificial Sequence
<220> FEATURE:
<223> OTHER INFORMATION: Consensus Sequence

<400> SEQUENCE: 6

Ile Gly Asp Ile Arg Gln Ala His Cys
1               5
```